US008841319B2

(12) United States Patent
Dannhardt et al.

(10) Patent No.: US 8,841,319 B2
(45) Date of Patent: Sep. 23, 2014

(54) USE OF 3-(INDOLYL)- OR 3-(AZAINDOLYL)-4-ARYLMALEIMIDE DERIVATIVES IN LEUKEMIA MANAGEMENT

(75) Inventors: Gerd Dannhardt, Mainz (DE); Thomas Fischer, Mainz (DE); Florian Heidel, Mainz (DE)

(73) Assignee: Johannes Gutenberg-Universitat Mainz, Mainz (DE)

( * ) Notice: Subject to any disclaimer, the term of this patent is extended or adjusted under 35 U.S.C. 154(b) by 412 days.

(21) Appl. No.: 12/746,630

(22) PCT Filed: Dec. 4, 2008

(86) PCT No.: PCT/EP2008/066776
§ 371 (c)(1),
(2), (4) Date: Oct. 25, 2010

(87) PCT Pub. No.: WO2009/071620
PCT Pub. Date: Jun. 11, 2009

(65) Prior Publication Data
US 2011/0028415 A1 Feb. 3, 2011

(30) Foreign Application Priority Data
Dec. 5, 2007 (EP) .................................... 07023588

(51) Int. Cl.
*A61K 31/40* (2006.01)
*A61K 31/44* (2006.01)

(52) U.S. Cl.
USPC .......................................... 514/300; 514/414

(58) Field of Classification Search
USPC ................................. 514/300, 414
See application file for complete search history.

(56) References Cited

FOREIGN PATENT DOCUMENTS

| WO | WO 02/38561 | 5/2002 |
|---|---|---|
| WO | WO 03/095452 | 11/2003 |
| WO | WO 03/103663 | 12/2003 |
| WO | WO 2004/094422 | 11/2004 |
| WO | WO 2006/061212 | 6/2006 |

OTHER PUBLICATIONS

Gove et al., Webster's Third New International Dictionary, 1963, p. 1798.*
"Leukemia", Merck Manual Online Edition, [retrieved on Oct. 23, 2012]. Retrieved from the Internet http://www.merckmanuals.com/home/print/. Revision Aug. 2012, 2 pages.*
Morissette, et al., Advanced Drug Delivery Reviews, 2004, 56, 275-300.*
Padro et al., Leukemia, 2002, 16, 1302-1310.*
Stone et al., Blood, 2005, 105, 54-60.*
Hussong et al., Blood, 2000, 95, 309-313.*
Byrn et al., solid state chemistry of drugs, publisdhed in 1999, 11 pages.*
International Preliminary Report on Patentability for PCT/EP2008/066776, 2010.
Peifer et al., "Profile and Molecular Modeling of 3-(Indole-3-yl)-4-(3,4,5-trimethoxyphenyl)-1*H*-pyrrole-2,5-dione (1) as a Highly Selective VEGF-R2/3 Inhibitor", J. Med. Chem., 2006, 49,7549-7553.
Pfeifer et al., "Design, Synthesis, and Biological Evaluation of 3,4-Diarylmaleimides as Angiogenesis Inhibitors", J. Med. Chem., 2006, 49, 1271-1281.
Routier et al., "Synthesis and Biological Evaluation of Novel Phenylcarbazoles as Potential Anticancer Agents", J. Med. Chem., 2006, 49, 789-799.
Heidel et al., "3,4-Diarylmaleimides—a novel class of kinase inhibitors—effectively induce apoptosis in FLT3-ITD-dependent cells", Ann Hematol, 91, 331-344 (2012).
Smith et al., "Validation of ITD Mutations in FLT3 as a Therapeutic Target in Human Acute Myeloid Leukaemia", Nature, vol. 485, 260-265 ( 2012).
Encyclopaedic Dictionary of Biology, S. Choudhary, "Chemotherapy", 3 pages (2003).
Webster's New World Medical Dictionary, Third Edition, "Chemotherapy", 3 pages (2008).

\* cited by examiner

*Primary Examiner* — Elli Peselev
(74) *Attorney, Agent, or Firm* — Viksnins Harris & Padys PLLP

(57) ABSTRACT

The present invention relates to the use of a compound of formula (I) wherein $R^1$ is H, $C_1$-$C_6$-alkyl, phenyl-$C_1$-$C_4$-alkyl or phenyl, $R^2$ is a phenyl group which is substituted with 2 or 3 $C_1$-$C_6$-alkoxy groups and $R^3$ is indolyl or azaindolyl which may carry one or two substituents independently selected from $C_1$-$C_6$-alkyl, $C_1$-$C_6$-alkoxy, phenyl, OH, halogen, $NH_2$, $C_1$-$C_6$-alkylamino, di-$C_1$-$C_6$-alkylamino, heteroaryl with 5 or 6 ring atoms containing 1 or 2 heteroatoms which are independently selected from O, N, and S, or heterocyclyl with 5 or 6 ring atoms containing 1 or 2 heteroatoms which are independently selected from O, N, and S, a physiologically acceptable salt thereof, or a solvate of the compound of formula (I) or of the salt thereof, for the prevention or treatment of leukemia.

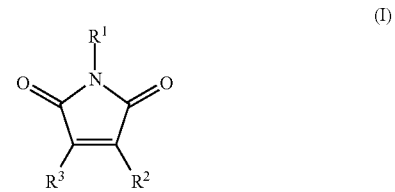

(I)

20 Claims, 11 Drawing Sheets

USE OF 3-(INDOLYL)- OR 3-(AZAINDOLYL)-4-ARYLMALEIMIDE DERIVATIVES IN LEUKEMIA MANAGEMENT

RELATED APPLICATIONS

This application is a National Stage application under 35 U.S.C. §371 of International Application No. PCT/EP2008/066776 having an International Filing Date of 4 Dec. 2008, which application claims the benefit of priority of European Application Serial No. 07023588.2 filed on 5 Dec. 2007.

The present invention relates to the use of 3-(indolyl)- or 3-(azaindolyl)-4-arylmaleimide derivatives for the prevention or treatment of leukemia.

Leukemia is a malignant cancer of the bone marrow and blood. It is characterized by the uncontrolled growth of blood cells. The common types of leukemia are divided into four categories: acute or chronic myelogenous, involving the myeloid elements of the bone marrow, and acute or chronic lymphocytic, involving the cells of the lymphoid lineage.

Acute leukemia is a rapidly progressing disease that results in the massive accumulation of immature, functionless cells (blasts) in the marrow and blood. The marrow often can no longer produce enough normal red and white blood cells and platelets. Anemia, a deficiency of red cells, develops in virtually all leukemia patients. The lack of normal white cells impairs the body's ability to fight infections. A shortage of platelets results in bruising and easy bleeding. In contrast, chronic leukemia progresses more slowly and leads to unregulated proliferation and hence marked overexpansion of a spectrum of mature (differentiated) cells. In general, acute leukemia, unlike the chronic form, is potentially curable.

Standard treatment for leukemia usually involves chemotherapy and/or bone marrow transplantation and/or radiation therapy.

The two major types of bone marrow transplants are autologus (uses the patient's own marrow) and allogeneic (uses marrow from a compatible donor). Radiation therapy, which involves the use of high-energy rays, is usually given before bone marrow transplantation to kill all leukemic cells.

Chemotherapy in leukemia usually involves a combination of two or more chemotherapeutic agents. Some common combinations include cytarabine with either doxorubicin or daunorubicin or mitoxantrone or thioguanine, mercaptopurine with methotrexate, mitroxantrone with etoposide, asparaginase with vincristine, daunorubicin and prednisone, cyclophosphamide with vincristine, cytarabine and prednisone, cyclophosphamide with vincristine and prednisone, daunorubicin with cytarabine and thioguanine, and daunorubicin with vincristine and prednisone.

New treatments for leukemia also include the reversal of multidrug resistance, involving the use of agents which decrease the mechanisms allowing the malignant cells to escape the damaging effects of the antineoplastic agent (and leads to refractoriness or relapses); and biological therapy, involving the use of substances known as biological response modifiers (BRMs). These substances are normally produced in small amounts as part of the body's natural response to cancer or other diseases. Types of BRMs include monoclonal antibodies, in which toxins are attached to antibodies that react with the complementary antigen carried by the malignant cells; and cytokines (e.g. interferons, interleukins, colony-stimulating factors CSFs) which are naturally occurring substances that stimulate blood cell production and help restore blood cell counts more rapidly after treatment.

Treatment of leukemia is very complex and depends upon the type of leukemia. Tremendous clinical variability among remissions is also observed in leukemic patients, even those that occur after one course of therapy. Patients who are resistant to therapy have very short survival times, regardless of when the resistance occurs. Despite improvements in outcome with current treatment programs, the need to discover novel agents for the treatment of all types of leukemia continues.

It was an object of the present invention to provide an effective therapy for leukemia, especially acute leukemia, such as acute myeloid leukemia (AML).

WO 2006/061212 describes that certain 3-(indolyl)- or 3-(azaindolyl)-4-arylmaleimide derivatives are angiogenesis inhibitors and proposes their use for controlling angiogenesis and/or vascular dysfunction. WO 2006/061212 lists number of disorders which are associated with pathological angiogenesis or vascular dysfunction, in particular solid tumors.

It was a further object of the present invention to provide a new use of said 3-(indolyl)- or 3-(azaindolyl)-4-arylmaleimide derivatives.

Surprisingly, it has been found that certain 3-(indolyl)- or 3-(azaindolyl)-4-arylmaleimide derivatives capable of inducing apoptosis in leukemic cells.

The present invention relates to the use of a compound of formula I:

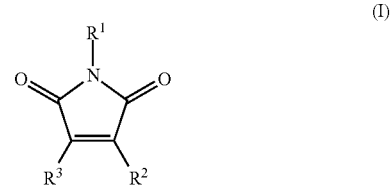

(I)

wherein
$R^1$ is H, $C_1$-$C_6$-alkyl, phenyl-$C_1$-$C_4$-alkyl or phenyl;
$R^2$ is a phenyl group which is substituted with 2 or 3 $C_1$-$C_6$-alkoxy groups, and
$R^3$ is indolyl or azaindolyl which may carry one or two substituents independently selected from $C_1$-$C_6$-alkyl, $C_1$-$C_6$-alkoxy, phenyl, OH, halogen, $NH_2$, $C_1$-$C_6$-alkylamino, di-$C_1$-$C_6$-alkylamino, heteroaryl with 5 or 6 ring atoms containing 1 or 2 heteroatoms which are independently selected from O, N, and S, or heterocyclyl with 5 or 6 ring atoms containing 1 or 2 heteroatoms which are independently selected from O, N, and S,
a physiologically acceptable salt thereof, or a solvate of the compound of formula I or of the salt thereof,
for the prevention or treatment of leukemia.

Thus, the present invention is concerned with compounds of Formula I, physiologically acceptable salts or solvates thereof for use in the treatment or prevention of leukemia. In particular, the present invention relates to the use of a compound of Formula I, a physiologically acceptable salt or solvate thereof as defined herein, in the manufacture of a medicament for preventing or treating leukemia.

The present invention also relates to a method of preventing or treating leukemia in a subject in need of such treatment, which comprises administering to said subject an amount therapeutically effective for preventing or treating leukemia, of a compound of Formula I, a physiologically acceptable salt or solvate thereof as defined herein.

Further, the present invention relates to a pharmaceutical composition comprising (i) a compound of formula I, a physiologically acceptable salt or solvate thereof as defined herein, and (ii) a further chemotherapeutic agent.

The term "leukemia" refers to a disease characterized by an abnormal proliferation (production by multiplication) of blood cells, usually white blood cells (leukocytes).

Leukemia includes acute and chronic forms.

Acute leukemia is characterized by the rapid proliferation of immature blood cells. This crowding makes the bone marrow unable to produce healthy blood cells. Acute forms of leukemia mostly occur in children and young adults.

Chronic leukemia is characterized by the excessive build up of relatively mature, but still abnormal, blood cells. Typically taking months to years to progress, the cells are produced at a higher rate than normal cells, resulting in abnormal white blood cells in the blood. Chronic leukemia mostly occurs in older people, but can theoretically occur in any age group.

Leukemia further includes lymphocytic (lymphoblastic) and myelogenous (myeloid) forms.

In lymphocytic or lymphoblastic leukemia, the cancerous change took place in a type of marrow cell that normally goes on to form lymphocytes including T cells (cytotoxic CD8+, Helper CD4+/Regulatory, yb, natural killer T cells); B cells (plasma and memory cells); or natural killer cells (lymphokine-activated killer cell).

In myelogenous or myeloid leukemia, the cancerous change took place in a type of marrow cell that normally goes on to form red cells (reticulocytes and normoblasts); some types of white cells (granulocytes (neutrophil, eosinophil, basophil), mast cell precursors, dendritic cells (Langerhans cells, follicular dendritic cells), monocytes/macrophages (histiocytes, Kupffer cells, Langhans giant cells, microglia, osteoclasts); megakaryoblasts; megakaryocytes; or platelets.

Thus, leukemia according to the present invention comprises in particular acute lymphocytic leukemia (also known as acute lymphoblastic leukemia, or ALL), acute myelogenous leukemia (also known as acute myeloid leukemia, or AML); chronic lymphocytic leukemia (CLL), and chronic myelogenous leukemia (CML). These leukemias and further subtypes of these leukemias are defined by morphological, histochemical and immunological techniques that are well known by those skilled in the art.

In a preferred embodiment, the invention relates to the treatment of AML or ALL.

The term "treatment of leukemia" includes partial or total inhibition of leukemia in a subject, as well as partial or total destruction of the leukemic cells.

The term "prevention of leukemia" includes preventing the onset of clinically evident leukemia as well as preventing the onset of a preclinically evident stage of leukemia in subjects at risk. Also intended to be encompassed by this definition is the prevention of initiation for leukemic cells or to arrest or reverse the progression of pre-leukemic cells to leukemic cells. This includes prophylactic treatment of those at risk of developing leukemia. The prevention of leukemia in particular includes the treatment of myelodysplastic syndrome (MDS).

As used herein, the term "subject" for purposes of treatment includes any mammalian, preferably human, subject who has or may have any form of leukemia. For methods of prevention, the subject is any mammal, preferably human, subject at risk for developing leukemia, e.g., a subject who has or may have MDS.

As used herein, the term "being at risk" refers to having a risk that is higher, preferably significantly higher, of developing leukemia than the majority of its peerage group defined by basic medical factors such as age, gender, weight, etc., well-known to the skilled person. The subject may be at risk due to exposure to carcinogenic agents, e.g. ionizing radiation or chemical mutagens, genetic predisposition to develop leukemia, and the like.

In a further preferred embodiment, the invention relates to the treatment of refractory leukemia, in particular refractory AML or ALL. As used herein, the term "refractory" is used to describe leukemia treated with currently available leukemia therapies such as chemotherapy, radiation therapy, and/or bone marrow transplantation, wherein the therapy is not clinically adequate to treat the subject such that these subjects need additional effective therapy, e.g., remain unsusceptible to therapy. The term can also describe subjects who respond to therapy yet suffer from side effects, relapse, develop resistance, etc. In various embodiments, "refractory" means that at least some significant portion of the leukemic cells is not killed or their cell division not arrested (also referred to as minimal residual disease, MRD). The determination of whether leukemia is "refractory" can be made either in vivo or in vitro by any method known in the art for assaying the effectiveness of treatment on leukemic cells, using the art-accepted meanings of "refractory" in such a context.

In a further preferred embodiment of the invention, leukemia is resistant leukemia and in particular multidrug resistant leukemia, i.e., the leukemic cells exhibit resistance to conventional chemotherapeutics, preferably the MDR (multi-drug resistance) phenotype. The term "resistance to" is herein used to refer to any significant increase in the required dosage of a chemotherapeutic agent, compared to the parental tissue which the neoplastic growth is derived from. The term "multidrug resistance" is used herein to refer to resistance caused by overexpression of the MDR protein (gp170), which is capable of clearing the cell of various types of chemotherapeutic agents, such as, e.g., doxorubicin.

In a further preferred embodiment of the invention, the leukemia is characterized by leukemic cells which are positive for expression of FLT3. In a particular embodiment of the invention, the leukemia is characterized by leukemic cells which show enhanced expression of FLT3, compared to non-malignant cells of the same cell type.

As used herein, the term "FLT3" denotes a receptor tyrosine kinase type III, i.e., fms-like tyrosine kinase receptor-3 (also known as fetal liver kinase-2 (FLK2) or CD135). When this receptor binds to its ligand it forms a dimer with itself (homodimer) which activates signaling through second messengers. Signaling through FLT3 plays a role in cell survival, proliferation, and differentiation. FLT3 is important for lymphocyte (B cell and T cell) development. FLT3 is known as a proto-oncogene.

The term "positive for expression" is used herein to denote presence of the FLT3 protein, e.g. presence of the FLT3 protein in a Western blot, of the mRNA transcript encoding the same, e.g. presence of the FLT3 mRNA transcript in a Northern blot or RT-PCR assay, or presence of the biochemical activity of FLT3, e.g. its phosphorylation activity. The term "enhanced expression" refers to a level of expression (protein, mRNA or activity) that is higher than control (e.g., as compared to non-malignant cells of the same cell type).

Mutations of FLT3 can lead to the development of leukemia. Mutations of FLT3 have been detected in about 30% of patients with acute myelogenous leukemia (AML) and a number of patients with acute lymphomatic leukemia (ALL) or myelodysplastic syndrome (MDS). Patients with FLT3 mutations tend to have a poor prognosis, with decreased remission times and disease free survival. Known types of activating mutations of FLT3 (leading, in particular, to constitutive receptor activation, especially constitutive receptor dimerization and/or constitutive receptor phosphorylation) include duplications of 4-40 amino acids in the juxtamembrane region (ITD mutation) of the receptor (25-30% of patients) and point mutations in the kinase domain (5-7% of patients). Expression of a mutant FLT3 receptor in murine marrow cells results in a lethal myeloproliferative syndrome (Kelly, L. M., Liu, Q., Kutok, J. L., Williams, I. R., Boulton, C. L. & Gilliland, D. G. (2002) FLT3 internal tandem duplication mutations associated with human acute myeloid leukemias induce myeloproliferative disease in a murine bone marrow transplant model. Blood, 99, 310-318), and preliminary studies (Gilliland et al., Blood. 2002; 100: 1532-42) suggest that mutant FLT3 cooperates with other leukemia oncogenes to confer a more aggressive phenotype.

Thus, in a further preferred embodiment of the invention, the leukemic cell is positive for one or more than one activating mutation in the FLT3 gene. Such mutations include, but are not limited to, the internal tandem duplication in the juxtamembrane domain of the FLT3 gene (FLT3-ITD-positive); activating loop mutations in the tyrosine kinase domain of the FLT3 gene, such as a substitution of aspartic acid for another amino acid at position 835 (D835X: Yamamoto, Y., Kiyoi, H., Nakano, Y., Suzuki, R., Kodera, Y., Miyawaki, S., Asou, N., Kuriyama, K., Yagasaki, F., Shimazaki, C., Akiyama, H., Saito, K., Nishimura, M., Motoji, T., Shinagawa, K., Takeshita, A., Saito, H., Ueda, R., Ohno, R. & Naoe, T. (2001) Activating mutation of D835 within the activation loop of FLT3 in human hematologic malignancies. *Blood*, 97, 2434-2439; and Frohling, S., Schlenk, R. F., Breitruck, J., Benner, A., Kreitmeier, S., Tobis, K., Dohner, H. & Dohner, K. (2002) Prognostic significance of activating FLT3 mutations in younger adults (16 to 60 years) with acute myeloid leukemia and normal cytogenetics: a study of the AML Study Group Ulm. *Blood*, 100, 4372-4380), a deletion of isoleucine at position 836, a substitution of isoleucine for threonine at position 836 or a substitution/insertion of isoleucine for methionine/arginine at position 836 (Thiede, C., Steudel, C., Mohr, B., Schaich, M., Schakel, U., Platzbecker, U., Wermke, M., Bornhauser, M., Ritter, M., Neubauer, A., Ehninger, G. & Illmer, T. (2002) Analysis of FLT3-activating mutations in 979 patients with acute myelogenous leukemia: association with FAB subtypes and identification of subgroups with poor prognosis. Blood, 99, 4326-4335), an insertion between positions 840 and 841 (840GS: Spiekermann, K., et al. (2002) A new and recurrent activating length mutation in exon 20 of the FLT3 gene in acute myeloid leukemia. *Blood*, 100, 3423-3425); a substitution of asparagine for isoleucine at position 841 (N841I: Jiang, J., et al. (2004) Identifying and chracterizing a novel activating mutation of the FLT3 tyrosine kinase in AML. *Blood*, 104, 1855-1858); a substitution of tyrosine for cysteine at position 842 (Y842C: Kindler, T., Breitenbuecher, F., Kasper, S., Estey, E., Giles, F., Feldman, E., Ehninger, G., Schiller, G., Klimek, V., Nimer, S. D., Gratwohl, A., Choudhary, C. R., Mueller-Tidow, C., Serve, H., Gschaidmeier, H., Cohen, P. S., Huber, C. & Fischer, T. (2005) Identification of a novel activating mutation (Y842C) within the activation loop of FLT3 in patients with acute myeloid leukemia (AML). *Blood*, 105, 335-340); a substitution of asparagine for lysine at position 676 (N676K: Heidel, F., Solem, F. K., Breitenbuecher, F., Lipka, D. B., Kasper, S., Thiede, M. H., Brandts, C., Serve, H., Roesel, J., Giles, F., Feldman, E., Ehninger, G., Schiller, G. J., Nimer, S., Stone, R. M., Wang, Y., Kindler, T., Cohen, P. S., Huber, C. & Fischer, T. (2006) Clinical resistance to the kinase inhibitor PKC412 in acute myeloid leukemia by mutation of Asn-676 in the FLT3 tyrosine kinase domain. Blood, 107, 293-300); and activating point mutations in the juxtamembrane domain, such as V592A, V579A, F594L, F590GY591 D (Reindl, C., Bagrintseva, K., Vempati, S., Schnittger, S., Ellwart, J. W., Wenig, K., Hopfner, K. P., Hiddemann, W. & Spiekermann, K. (2006) Point mutations in the juxtamembrane domain of FLT3 define a new class of activating mutations in AML. *Blood*, 107, 3700-3707).

The term "positive for a mutation" is used herein to denote presence of the corresponding mutated nucleic acid, e.g. mutated DNA or mRNA in an assay such as DNA sequencing, sequencing by hybridization, SSCP (single strand conformational analysis), DGGE (denaturing gradient gel electrophoresis), TGGE (temperature gradient gel electrophoresis), Cleavase, Heteroduplex analysis, CMC (chemical mismatch cleavage), enzymatic mismatch cleavage, solid phase hybridization (dot blots, MASDA, reverse dot blots, oligonucleotide arrays (chips)), solution phase hybridization (Taqman, Molecular Beacons), ARMS (Amplification Refractory Mutation System), ALEX (Amplification Refractory Mutation System Linear Extension), SBCE (Single Base Chain Extension), Mini-sequencing, APEX, (Arrayed Primer Extension), RFLP (restriction fragment length polymorphism), OLA (Oligonucleotide Extension Assay) and other techniques, as is known in the art.

Primer sequences and amplification protocols for evaluating FLT3 (FLK2) mutations are known to those in the art and have been published in, e.g., Nakao, M., et al., 1996, supra; Yamamoto, Y., et al., 2001, supra; Fröhling, S., et al., 2002, supra; Thiede, C., et al., 2002, supra; Kindler, T., et al., 2005, supra; Reindl, C., et al., 2006, supra; Heidel, F., et al., 2006, supra; Jiang, J., et al., 2004, supra; Spiekermann, K., et al., 2002, supra; Gilliland et al., Curr. Opin., Hematol., 9:274-281 (2002); and Gilliland et al., 2002, supra.

According to a particularly preferred embodiment, the invention relates to the treatment of FLT3-ITD-positive AML or FLT3-ITD-positive ALL, or its prevention, e.g. by treating FLT3-ITD-positive MDS. According to a further particularly preferred embodiment, the invention relates to the treatment of FLT3-ITD-positive AML or FLT3-ITD-positive ALL, or its prevention, e.g. by treating FLT3-ITD-positive MDS, wherein the leukemic cells are also positive for a further activating mutation in the FLT3 gene, as defined above. In a particular embodiment, the invention relates to the treatment of FLT3-ITD- and N676K-positive AML or FLT3-ITD- and N676K-positive ALL, or its prevention, e.g. by treating FLT3-ITD- and N676K-positive MDS.

According to the invention, AML and ALL in particular include leukemia at primary diagnosis and leukemia after primary treatment (i.e., secondary leukemia), e.g., leukemia which is refractory (such as minimal residual leukemia) and/or resistant.

The term "alkyl", "alkoxy", "alkylamino" etc. denotes chemical radicals which include linear or branched alkyl groups having 1 to 6 and preferably 1 to 4 carbon atoms. Examples for alkyl groups are methyl, ethyl, n-propyl, i-propyl, n-butyl, sec-butyl, iso-butyl, t-butyl, n-pentyl or n-hexyl. Examples for alkoxy groups are methoxy, ethoxy, n-propoxy, isopropoxy, n-butoxy.

Halogen means F, Cl, Br and I, preferably F and Cl.

Heteroaryl means a 5- or 6-membered aromatic ring having 1 or 2 heteroatoms selected from O, N. and S. Examples for heteroaryl are thienyl, furyl, imidazolyl, pyrazolyl, thiazolyl, oxazolyl, pyridyl or pyrimidyl.

Heterocyclyl means a 5- or 6-membered saturated or unsaturated, non-aromatic ring having 1 or 2 heteroatoms selected from O, N, and S. Examples for heterocyclyl are pyrrolidinyl, tetrahydrofuranyl, imidazolinyl, imidazolidinyl, piperidinyl, morpholinyl.

Physiologically acceptable salts of the compounds of formula I include acid addition salts with inorganic acids, such as hydrochloric acid, sulfuric acid, or phosphoric acid, or with organic acids, in particular carboxylic acids, such as acetic acid, tartaric acid, lactic acid, citric acid, maleic acid, amygdalic acid, ascorbic acid, fumaric acid, gluconic acid or sulfonic acids, such as methane sulfonic acid, benzene sulfonic acid and toluene sulfonic acid.

Physiologically acceptable solvates are in particular hydrates.

According to a particular embodiment, the present invention relates to the use of compounds of formula I wherein $R^2$ is a group having the formula

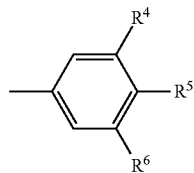

wherein two of the radicals $R^4$, $R^5$ and $R^6$ are $C_1$-$C_6$-alkoxy and the third of said radicals is H or $C_1$-$C_6$-alkoxy. Preferably, $R^4$ and $R^5$ are $C_1$-$C_6$-alkoxy and $R^6$ is hydrogen or $R^4$, $R^5$ and $R^6$ are $C_1$-$C_6$-alkoxy.

According to a further particular embodiment, the present invention relates to the use compounds of formula I wherein $R^3$ is selected from:

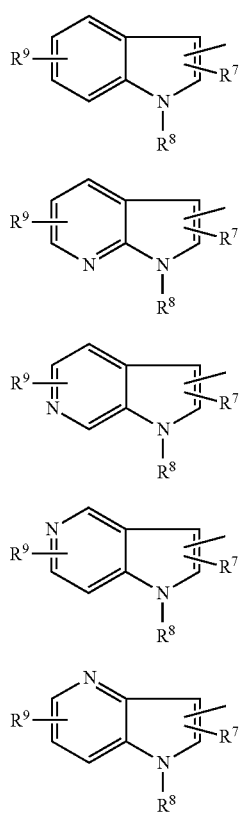

wherein $R^7$ is H, $C_1$-$C_6$-alkyl or phenyl, $R^8$ is H, $C_1$-$C_6$-alkyl or phenyl and $R^9$ is H, $C_1$-$C_6$-alkyl, $C_1$-$C_6$-alkoxy, OH, halogen, $NH_2$, $C_1$-$C_6$-alkylamino, di-$C_1$-$C_6$-alkylamino, heteroaryl with 5 or 6 ring atoms containing 1 or 2 heteroatoms which are independently selected from O, N, and S, or heterocyclyl with 5 or 6 ring atoms containing 1 or 2 heteroatoms which are independently selected from O, N, and S, preferably H, $C_1$-$C_6$-alkyl or $C_1$-$C_6$-alkoxy.

The indolyl or azaindolyl group, for example groups (a) to (e), are preferably attached to the maleimide group via the 3-position of the indolyl or azaindolyl group.

According to one embodiment, the present invention relates to the use of compounds of formula (Ia):

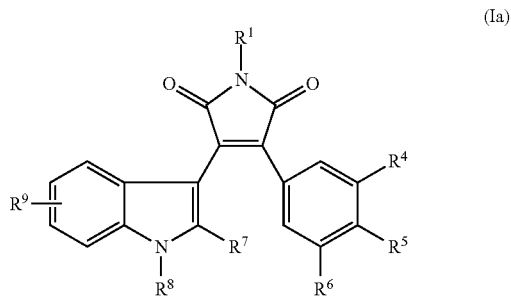

wherein $R^1$, and $R^4$ to $R^9$ have the meanings given above.

According to a further embodiment, the present invention relates to the use of compounds of formula (Ib):

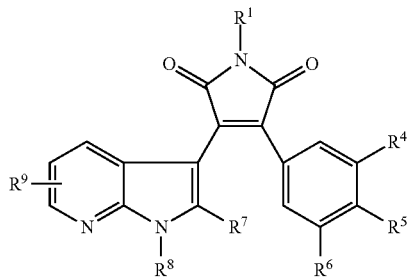

wherein $R^1$, and $R^4$ to $R^9$ are as defined above.

According to a further embodiment, the present invention relates to the use of compounds of formula (Ic):

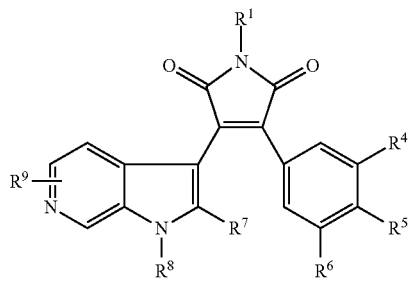

wherein $R^1$, and $R^4$ to $R^9$ are as defined above.

According to a further embodiment, the present invention relates to the use of compounds of formula (Id):

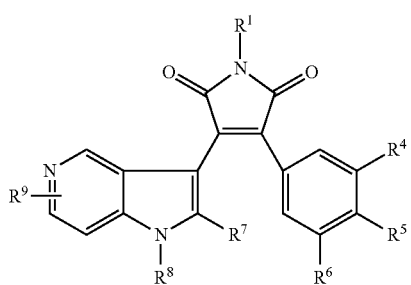

(Id)

wherein $R^1$, and $R^4$ to $R^9$ are as defined above.

According to a further embodiment, the present invention relates to the use compounds of formula (Ie):

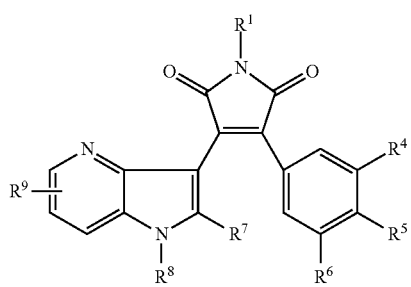

(Ie)

wherein $R^1$, and $R^4$ to $R^9$ are as defined above.

According to a further embodiment, $R^1$, $R^7$, $R^8$ and $R^9$ are independently of each other H or $C_1$-$C_6$-alkyl, and in particular, $R^1$, $R^7$, $R^8$, and $R^9$ are H.

Particular compounds of Formula I include the following:
3-(Indole-3-yl)-4-(3,4,5-trimethoxyphenyl)-1H-pyrrole-2,5-dione (also referred to herein as DHF125);
3-(Indole-3-yl)-4-(3,4-dimethoxyphenyl)-1H-pyrrole-2,5-dione;
3-(5-Methoxyindole-3-yl)-4-(3,4,5-trimethoxyphenyl)-1H-pyrrole-2,5-dione;
3-(1-Methylindole-3-yl)-4-(3,4,5-trimethoxyphenyl)-1H-pyrrole-2,5-dione;
3-(2-Methylindole-3-yl)-4-(3,4,5-trimethoxyphenyl)-1H-pyrrole-2,5-dione;
3-(2-Phenylindole-3-yl)-4-(3,4,5-trimethoxyphenyl)-1H-pyrrole-2,5-dione;
3-(Indole-2-yl)-4-(3,4,5-trimethoxyphenyl)-1H-pyrrole-2,5-dione;
3-(7-Azaindol-3-yl)-4-(3,4,5-trimethoxyphenyl)-1H-pyrrole-2,5-dione (also referred to herein as DHF150);
3-(6-Azaindol-3-yl)-4-(3,4,5-trimethoxyphenyl)-1H-pyrrole-2,5-dione;
3-(5-Azaindol-3-yl)-4-(3,4,5-trimethoxyphenyl)-1H-pyrrole-2,5-dione,
the physiologically acceptable salts thereof, and the solvates of the compounds of formula I or of the salts thereof.

The compounds of the present invention can be prepared according to known methods, for example according to the methods, which are disclosed in WO 02/38561, EP 328 026, WO 03/095452 and WO 2006/061212.

It is particularly preferred if the subject to be treated will not benefit from conventional therapy, e.g. as defined above, in the absence of pharmacotherapy comprising the administration of compounds of Formula I, physiologically acceptable salts or solvates thereof, the term "benefit" herein being used to denote the attainment of any or all of the objects of treatment or prevention as defined above.

Thus, very effective compounds of Formula I are those which, or whose physiologically acceptable salts or solvates, stimulate apoptosis in leukemic cells. The term "stimulate" is used herein to denote any inducing or promoting effect. The term "induce" is used herein to denote any significant increase in the rate of apoptosis in cells treated with compounds of Formula I, physiologically acceptable salts or solvates thereof, compared to cells kept under otherwise identical conditions but not treated with compounds of Formula I, physiologically acceptable salts or solvates thereof. The term "promote" is used herein to denote any significant increase in the rate of apoptosis in cells treated with compounds of Formula I, physiologically acceptable salts or solvates thereof and one or more than one further agent or agents compared to cells kept under otherwise identical conditions including the further agent or agents but not the compounds of Formula I, physiologically acceptable salts or solvates thereof.

Suitable compounds can be identified among the compounds of Formula I, physiologically acceptable salts or solvates thereof using well-known screening procedures such as high-throughput screening (HTS) procedures. A typical procedure comprises testing the cellular readiness for apoptosis by each of a number of candidate compounds of Formula I, physiologically acceptable salts or solvates thereof, and identifying those which have the desired activity. At a higher level of screening, the suitability for prevention and/or treatment of leukemia in general, and/or of individual forms of leukemia in particular, may be investigated using animals model known to the skilled artisan.

In a particular embodiment of the invention, the treatment of the subject comprises further stimulation of cell death by a conventional method or combination of conventional methods, the conventional methods preferably being selected from the group consisting of irradiation, e.g. external irradiation or administration of radioactive compounds, bone marrow transplantation and treatment with a chemotherapeutic agent including antineoplastic agents, multidrug resistance reversing agents; and biological response modifiers, and combinations thereof, examples being given below.

The present invention thus also relates to the use of a 3-(indolyl)- or 3-(azaindolyl)-4-phenylmaleimide derivative of formula I, a physiologically acceptable salt or solvate thereof as defined herein in combination with one or more than one further chemotherapeutic agent.

Suitable antineoplastic agents may be selected from the group consisting of asparaginase, bleomycin, busulfan, carmustine, chlorambucil, cladribine, cyclophosphamide, cytarabine, dacarbazine, daunorubicin, doxorubicin, etoposide, fludarabine, gemcitabine, hydroxyurea, idarubicin, ifosfamide, lomustine, mechlorethamine, melphalan, mercaptopurine, methotrexate, mitomycin, mitoxantrone, pentostatin, procarbazine, 6-thioguanine, topotecan, vinblastine, vincristine, dexamethasone, retinoic acid and prednisone.

Particularly preferred examples for antineoplastic agents to be used in the treatment of leukemia, especially AML or ALL, comprise cytarabine, etoposide, mitoxantron, cyclophosphamide, retinoic acid, daunorubicin, doxorubicin and idarubicin.

An example for a multidrug resistance reversing agent is PSC 833.

Suitable biological response modifiers may be selected from the group consisting of monoclonal antibodies and cytokines, such as interferons, interleukins and colony-stimulating factors, e.g., rituxan, CMA-676, interferon-alpha recombinant, interleukin-2, interleukin-3, erythropoetin, epoetin, G-CSF, GM-CSF, filgrastim, sargramostim and thrombopoietin.

The present invention is based, in part, on the recognition that the compounds of formula I, physiologically acceptable salts and solvates thereof potentiate and synergize with, enhance the effectiveness of, improve the tolerance of, and/or reduce side effects caused by, other leukemia therapies, including current standard and experimental chemotherapies, bone marrow transplants, stem cell replacement therapies and radiation therapies. Thus, the invention encompasses treatment regimens or protocols that provide better therapeutic profiles than current single agent therapies or current combination therapy regimens. Encompassed by the invention are combination therapies that have additive potency or an additive therapeutic effect. The invention also encompasses synergistic combinations where the therapeutic ratio is greater than additive. Preferably, such combinations also reduce or avoid unwanted or adverse effects. In certain embodiments, the combination therapies encompassed by the invention provide an improved overall therapy relative to administration of either a compound of formula I, a physiologically acceptable salt or solvate thereof or any other leukemia therapy alone. Given the invention, in certain embodiments, doses of existing or experimental leukemia therapies can be reduced or administered less frequently which increases patient compliance, improves therapy and reduces unwanted or adverse effects.

Accordingly, the present invention relates to pharmaceutical compositions comprising (i) a compound of formula I, a physiologically acceptable salt or solvate thereof as defined herein, and (ii) a further chemotherapeutic agent.

The present invention also relates to methods of preventing or treating leukemia, and pharmaceutical compositions useful therein as well as suitable packaging for the same, which are especially applicable to mammals, e.g. humans, which suffer from or in the future may suffer from leukemia. In a preferred embodiment of the invention, the subject is a human at increased risk of leukemia as defined above. It is particularly preferred if the subject is a human suffering from leukemia as defined above.

In accordance with the present invention, preventing or treating leukemia in a subject in need of such treatment, comprises administering to said subject an amount therapeutically effective for preventing or treating leukemia, of one or more than one compound of Formula I, a physiologically acceptable salt or solvate thereof.

The expression "preventing or treating" as used herein with reference to the administration of the compounds of the present invention, is intended to refer to both the therapeutic objective of said administration as well as the therapeutic results actually achieved by said administration. As discussed above, the extent of therapy accomplished by administration of said compounds may range from an amelioration to a significant diminishing of the course of the disease, and beyond to active treatment of the disease, including a reversal of the disease process.

The compounds of Formula I, physiologically acceptable salts or solvates thereof, of the present invention may also be combined with further therapeutically active ingredients which would be readily apparent to the skilled artisan in this field, and which will usually be determined by the circumstances under which the therapeutic agent of the present invention is administered. Examples of such other therapeutically active ingredients include, but are not limited to the above agents.

In accordance with a regimen which would be used according to the invention, it is contemplated that the compounds of Formula I, physiologically acceptable salts or solvates thereof would be administered in combination with other medications used on a regularly scheduled basis. It is also envisioned that administration in combinations could assume a number of different forms and still be within the scope of the present invention. E. g., the compounds of Formula I, physiologically acceptable salts or solvates thereof might simply be formulated with one or more of the other therapeutic agents which are to form the intended combination, into a convenient dosage form, such as an oral tablet, containing all of the drugs forming the combination. Varying half-lives for the different drugs could be accommodated by the person skilled in preparing formulations by creating controlled-release forms of said drugs with different release times so that relatively uniform dosing is achieved, or by designing a time-adjusted formulation sequence in which different formulations with suitably varied dosages of the individual compounds are combined for scheduled administration, e.g. a formulation sequence which comprises distinct formulations for hourly, twice-a-day and daily administration. The present invention also contemplates co-administration in which the combination of drugs is achieved by the simultaneous administration of the drugs to be given in combination. Such co-administration could even be by means of different dosage forms and routes of administration. The present invention further contemplates the use of such combinations in accordance with different but regular and continuous dosing schedules whereby desired plasma levels of the drugs involved are maintained in the subject being treated, even though the individual drugs making up the combination are not being administered to said subject simultaneously. All such combinations would be well within the skill of the artisan to devise and administer.

When the compounds of Formula I, physiologically acceptable salts or solvates thereof are to be used as active ingredients in the uses, methods and compositions of the present invention, they can be incorporated into standard pharmaceutical dosage forms, which the skilled artisan is familiar with. Basically, any pharmaceutical dosage form may be used in the invention.

The present invention thus also relates to pharmaceutical compositions comprising a pharmaceutically acceptable auxiliary agent in addition to a compound of Formula I, a physiologically acceptable salt or solvate thereof as above-defined. Such auxiliary agents are known in the art. e.g., the usual pharmaceutical excipients, diluents and adjuvants, e.g., organic and inorganic inert carrier materials such as water, gelatine, lactose, starch, magnesium stearate, talc, vegetable oils, gums, polyalkylene glycols, etc. These pharmaceutical preparations can be employed in a solid form, e.g., as tablets, capsules, or they can be administered in liquid form, e.g., as solutions, suspensions or emulsions.

Further pharmaceutical excipients and adjuvants which may be added include preservatives, antioxidants, antimicrobial agents and other stabilizers; wetting, emulsifying and suspending agents, and anti-caking compounds; fragrance and colouring additives; compositions for improving compressibility, or agents to create a delayed, sustained or controlled release of the active ingredient; and various salts to change the osmotic pressure of the pharmaceutical preparation or to act as buffers. Such excipients and adjuvants are known to the skilled artisan.

The therapeutically effective amount of a compound of Formula I, a physiologically acceptable salt or solvate thereof, as defined may be administered systemically to said subject, wherein said systemic administration comprises: (1) injection or infusion into suitable body tissues or cavities of a pharmaceutical composition containing said compound in suitable liquid form such as aqueous solutions, emulsions or suspensions for intraarterial, intra- or transdermal (including subcutaneous), or intraspinal, especially intrathecal, and most commonly for intramuscular or intravenous delivery thereof; or for serving as a depot for delivery thereof; (2) instillation into suitable body tissues or cavities of a pharmaceutical composition containing said compound in suitable solid form, e.g., comprising a matrix of bio-compatible and bio-erodible materials in which particles of a solid compound of Formula I, a physiologically acceptable salt or solvate thereof, are dispersed, or in which, possibly, globules or isolated cells of a liquid compound of Formula I, a physiologically acceptable salt or solvate thereof, are entrapped, for serving as a solid implant composition for delayed-, sustained-, and/or controlled-release delivery thereof; or (3) ingestion or administration of a pharmaceutical composition containing said compound in suitable solid or liquid form for transdermal delivery thereof, for instance a transdermal patch or a subepidermal (subcuticular) implant, for peroral delivery thereof.

Said therapeutically effective amount of a compound of Formula I, a physiologically acceptable salt or solvate thereof as defined may also be administered locally to said subject, wherein said local administration comprises: (1) injection or infusion into a local site of a pharmaceutical composition containing said compound of formula I, physiologically acceptable salt or solvate thereof in suitable liquid form for delivery thereof, including components which provide delayed-release, controlled-release, and/or sustained-release of said compound into said local site; or for serving as a depot for delivery thereof wherein said composition provides storage of said compound and thereafter delayed-, sustained-, and/or controlled-release thereof; or (2) instillation of a pharmaceutical composition containing said compound in suitable solid form for serving as a solid implant for delivery thereof, said composition optionally providing delayed-, sustained-, and/or controlled-release of said compound to said local site.

A substantial number of the dosage forms described herein may be formulated so as to provide controlled-, sustained-, and/or delayed release of the active ingredient from said dosage form.

In a particular embodiment of the invention, the formulation to be used is a formulation for targeted drug delivery, e.g. a formulation that increases the effective concentration of the drug in the tissue that has given rise to the leukemic cell, or more specifically in or around the leukemic cell itself. Examples for such targeted drug delivery systems comprise conjugates, liposomes, micelles and nanoparticulate structures, as known in the art.

Preferred peroral dosage forms for systemic administration are solids, e.g., palatable oral compositions such as tablets, capsules, caplets, etc., and liquids, e.g., solutions, suspensions, emulsions, etc.

Injections may also be made of pharmaceutical compositions containing the compound of Formula I, a physiologically acceptable salt or solvate thereof, where the pharmaceutical composition is in delayed-release, controlled-release, or sustained-release form. These formulations of recognized composition may be solids, semi-solids, gels or other liquid/solid combinations in which an erodible matrix or series of coatings is used to provide a continuous release of the compound of Formula I, the physiologically acceptable salt or solvate thereof at a predetermined rate or at variable rates if desired. The terms "extended-release" and "long-acting" as well as others are used to describe these formulations. All of these employ various combinations of bioerodible polymers, e.g., various cellulosic polymers, and natural materials, e.g., corn starch and magnesium stearate, to obtain slow and/or uniform dispensing of the compound of Formula I, a physiologically acceptable salt or solvate thereof contained within the matrix.

The therapeutically effective amount for preventing or treating leukemia, of the compound of Formula I, a physiologically acceptable salt or solvate thereof, is administered to a subject being treated in an amount expressed as milligrams per kilogram of body weight of said subject, per day: "mg/kg/day". The expression "per day" as used herein should not be interpreted as necessarily requiring that any particular dosage form be administered on a daily basis to the subject being treated. The expression "per day" is merely an indication of the smallest convenient but arbitrary segment of time which is being used as part of the overall unit for measuring the dose of effective compound being administered. Depending on the route of application and other details, the daily dosage may be split into a number of sub-doses for subsequent administration in regular intervals, or, when using sustained or controlled release, several daily dosages may be joined into a single depot dosage.

The dose, i.e., the therapeutically effective amount of a compound of Formula I, a physiologically acceptable salt or solvate thereof for preventing or treating leukemia will usually range from about 0.1 mg/kg/day to about 20.0 mg/kg/day, preferably from about 0.1 mg/kg/day to about 12.0 mg/kg/day, more preferably from about 0.5 mg/kg/day to about 10.0 mg/kg/day, and most preferably from about 0.5 mg/kg/day to about 8.0 mg/kg/day. Particularities of absorption, metabolism and excretion characteristic for the respective tumour type, or found in an individual subject, will have to be taken into account.

It is also contemplated that in accordance with the present invention there will also be provided a package suitable for use in commerce for preventing or treating leukemia in a subject in need of such treatment, comprising a suitable outer carton and an inner container removably housed therein; enclosed in said container a suitable dosage form of a compound of Formula I, a physiologically acceptable salt or solvate thereof as described hereinabove; and associated with said carton or container printed instructional and informational material, which may be attached to said carton or to said container enclosed in said carton, or displayed as an integral part of said carton or container, said instructional and informational material stating in words which convey to a reader thereof that said active ingredient, when administered to a subject in a condition of leukemia will ameliorate, diminish, actively treat, reverse or prevent the condition. In a preferred embodiment said package comprising carton and container as above-described will conform to all regulatory requirements relating to the sale and use of drugs for the treatment of subjects, including especially said instructional and informational material.

The use and method of the present invention can be further defined to comprise two basic steps: (i) establishing, basically by means known to those skilled in the art, the status of a candidate subject as presently or prospectively being in a condition of leukemia, thereby confirming that said subject is in need of such treatment; and thereupon (II) preventing or treating said condition by administering to said subject an amount therapeutically effective for preventing or treating leukemia of a compound of Formula I, a physiologically acceptable salt or solvate thereof. The various aspects of Step (II) have already been discussed above in detail. Accordingly, the aspects of Step I will now be discussed in detail.

As far as diagnosis is concerned, it is expedient to establish the status of a subject which is a candidate for treatment in accordance with the present invention as to whether or not the subject is presently or prospectively in a condition of leukemia. The expression "presently or prospectively" as used herein is intended to mean that in accordance with the below-discussed methods of making that determination, it is possible to identify a candidate subject as either being presently in need of such treatment, or as very likely or expected to be in need of such treatment in the short term future. Prospective need of treatment may be established by those determinations of positive factors which from the experience of the artisan lead directly to the condition of disease related to leukemia. E. g., the artisan may establish from clinical examination of a subject that it has a condition of leukemia and may confirm this conclusion with further evidence from which it may be determined in accordance with established methods of measurement that the subject will develop leukemia within the short term future. In human subjects, established risk factors such as occupational exposure to mutagens, familial occurrence of FLT3-ITDs etc. may also be considered.

The status of said subject as presently or prospectively being in said condition of leukemia, and thus in need of such treatment, is in particular determined by positive results from the clinical examination and evaluation of samples of the candidate subject, e.g. by morphological, histochemical and immunological methods. Other clinical symptomology and signs would include those gained from direct examination of the condition of the candidate subject.

According to the present invention, a "sample" means any biological material containing diagnostically useful information in the form of cells, cell components, proteins or nucleic acids obtainable or obtained from an individual. The sample includes e.g. tissue samples, cell samples, bone marrow and/or body fluids such as blood, saliva, semen. Preferably, the sample is blood or bone marrow, more preferably the sample is bone marrow. The person skilled in the art is aware of methods, how to obtain a sample and to isolate nucleic acids and proteins from a sample. A diagnostic method using such a sample is usually an in vitro method.

Usually, a method of diagnosing leukemia comprises an analysis of the cytomorphology and cytochemistry of bone marrow blasts and peripheral blood cells. If required, immunophenotyping can be used, e.g., to separate undifferentiated AML from acute lymphoblastic leukemia and CLL. Optionally, a genetic analysis based on chromosome analysis, fluorescence in situ hybridization or RT-PCR and immunophenotyping is performed to assign all cases in to the right category.

In 1976, the FAB classification was proposed by the French-American-British co-operative group which was based on cytomorphology and cytochemistry in order to separate acute leukemia subgroups according to the morphological appearance of blasts in the blood and bone marrow (L1, L2 or L3 for ALL, and M1, M2, M3, M4, M5, M6 or M7 for AML). In addition, it was recognized that genetic abnormalities occurring in the leukemic blasts had a major impact on the morphological picture and even more on the prognosis.

Using these techniques alone or in combination, a first step comprises separating hematological malignancies into chronic myeloid leukemia (CML), chronic lymphatic (CLL), acute lymphoblastic (ALL), and acute myeloid leukemia (AML).

Within the latter three disease entities several prognostically relevant subtypes have been established. Thus, a second step may follow which comprises further sub-classification based on genetic abnormalities of the leukemic blasts. This step may comprise karyotyping leukemic cells or performing further genetic analyses (genotyping).

For diagnostic purposes, it may also be found expedient to perform in vitro testing, e.g. for determining the sensitivity of an individual leukemic growth to a treatment with a compound of Formula I, a physiologically acceptable salt or solvate thereof or composition containing the same, as defined above. For example, an appropriate sample may be subjected to various concentrations of the compounds and/or compositions of the invention and assayed for reaction. In vitro, apoptosis can be measured by any of a number of methods which the skilled artisan is familiar with. The data thus obtained may serve as a basis for rationally determining dosage and route of application to be used.

The skilled artisan will appreciate that treatment according to the present invention may also be combined with any suitable non-pharmacological treatment.

BRIEF DESCRIPTION OF THE DRAWINGS

FIG. 4 shows the percentage of apoptotic cells on top of ground apoptosis in primary AML blasts at primary diagnosis upon 72 h incubation with DHF125 and DHF150.

DESCRIPTION OF PREFERRED EMBODIMENTS

Figure 1A:
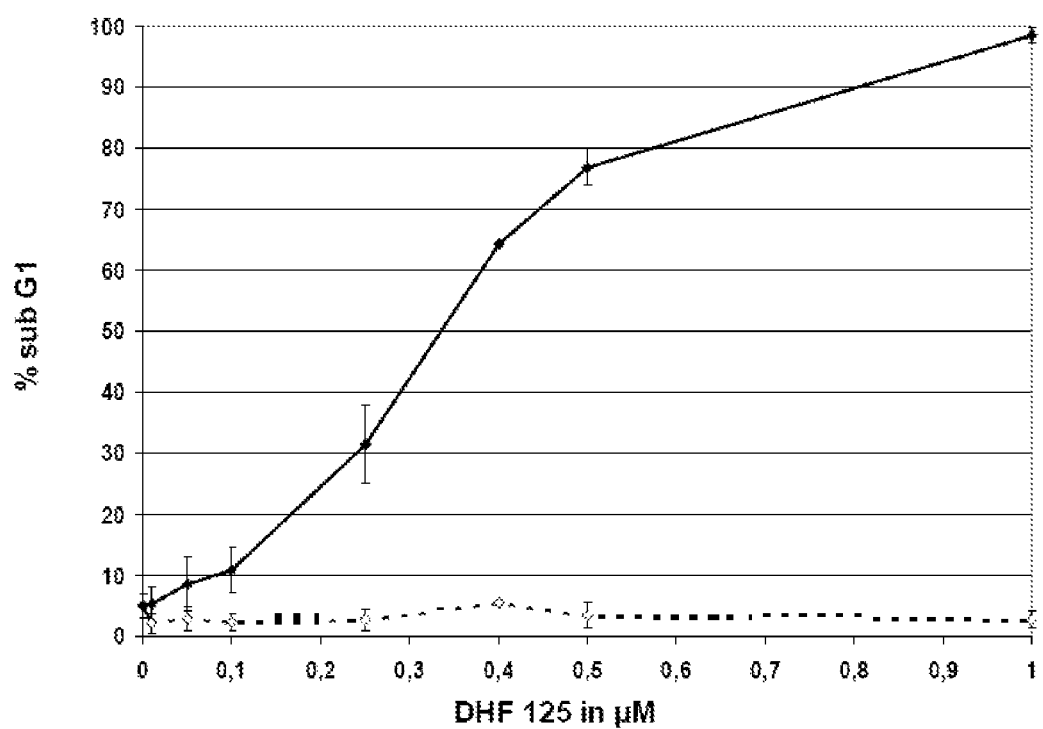
FIG. 1 shows the percentage of the sub-G1-cell fraction of murine 32D-FLT3-ITD cells (A and B) or FLT3-WT cells (C) upon 48 h incubation with DHF125 and DHF150.

In order to further demonstrate the uses, methods and compositions of the present invention, there is presented in the paragraphs which follow specific descriptive examples of typical procedures which may be employed in carrying out said methods. However, said examples are intended to be illustrative only and should not be taken as in any way a limitation of the present invention, for which purpose the present claims are appended hereto.

EXAMPLES

The effects of an 3-(indolyl)- and a 3-(azaindolyl)-4-phenylmaleimide derivatives, 3-(indole-3-yl)-4-(3,4,5-trimethoxyphenyl)-1H-pyrrole-2,5-dione (also referred to as DHF 125) and 3-(7-azaindol-3-yl)-4-(3,4,5-trimethoxyphenyl)-1H-pyrrole-2,5-dione (also referred to as DHF150), on the proliferation of FLT3-ITD transfected 32D leukemic cells as well as primary ITD-positive AML blasts were investigated.

Materials & Methods

DNA Constructs and Generation of Transfected Cells

A human FLT3-ITD construct, subcloned into the pAL expression vector under control of the 5' long terminal repeat (LTR) of the Moloney murine sarcoma virus (MoMSV) and the plasmid pMAM/BSD were used as previously described (Mizuki, M., Schwable, J., Steur, C., Choudhary, C., Agrawal, S., Sargin, B., Steffen, B., Matsumura, I., Kanakura, Y., Bohmer, F. D., Muller-Tidow, C., Berdel, W. E. & Serve, H. (2003) Suppression of myeloid transcription factors and induction of STAT response genes by AML-specific FLT3 mutations. *Blood*, 101, 3164-3173). The N676K point mutation was introduced into this FLT3-ITD construct (Medigenomix Martinsried, Germany). Vector constructs were confirmed by nucleotide sequencing and transfected into murine 32D cells as previously described (Heidel, F., Solem, F. K., Breitenbuecher, F., Lipka, D. B., Kasper, S., Thiede, M. H., Brandts, C., Serve, H., Roesel, J., Giles, F., Feldman, E., Ehninger, G., Schiller, G. J., Nimer, S., Stone, R. M., Wang, Y., Kindler, T., Cohen, P. S., Huber, C. & Fischer, T. (2006) Clinical resistance to the kinase inhibitor PKC412 in acute myeloid leukemia by mutation of Asn-676 in the FLT3 tyrosine kinase domain. *Blood*, 107, 293-300).

Murine BaF3 cells were transfected with an FLT3-ITD construct, subcloned into the MigRI expression vector. Mutagenesis was performed as previously described (Kancha, R. K., Grundler, R., Peschel, C. & Duyster, J. (2007) Sensitivity toward sorafenib and sunitinib varies between different activating and drug-resistant FLT3-ITD mutations. *Exp Hematol*, 35, 1522-1526).

Cells were cultured in RPMI 1640 with 10% FCS supplemented with 20 mM Hepes (pH 7.3), 50 mM β-mercaptoethanol and 2 mM L-glutamine.

Protein Extract Preparation and Western Blotting $2 \times 10^6$ cells were incubated in the presence of various inhibitor concentrations alone and in combination for 1 hour at 37° C. Preparation of cellular lysates was performed as described previously (Kindler, T., Breitenbuecher, F., Kasper, S., Estey, E., Giles, F., Feldman, E., Ehninger, G., Schiller, G., Klimek, V., Nimer, S. D., Gratwohl, A., Choudhary, C. R., Mueller-Tidow, C., Serve, H., Gschaidmeier, H., Cohen, P. S., Huber, C. & Fischer, T. (2005) Identification of a novel activating mutation (Y842C) within the activation loop of FLT3 in patients with acute myeloid leukemia (AML). *Blood*, 105, 335-340). Protein lysates were subjected to SDS polyacrylamid gel electrophoresis (SDS-PAGE) and blotted onto nitrocellulose membrane (Amersham, Freiburg, Germany) as previously described (Kindler, et al 2003). The following antibodies were used: anti-phospho-FLT3, anti-phospho-STAT5 (pTyr694/699), anti-phospho AKT (pSer473), anti-phospho ERK (pThr202/pTyr204) (all Cell Signaling Technology™, Frankfurt, Germany), anti-FLT3, anti-AKT and anti-STAT5 (Santa Cruz, Heidelberg, Germany), and anti-β-Actin (ICN). Densitometric analysis was performed using the program Gel-Pro Analyzer®.

Apoptosis Assay by Cell Cycle Analysis

Transfected murine 32D cells ($1 \times 10^5$ cells/well) were incubated in 2 ml RPMI medium supplemented with 10% FCS with different inhibitor concentrations for 48 hours at 37° C. Primary human cells ($2 \times 10^5$ cells/well) were incubated for 72 hours at 37° C. After incubation, cells were washed with ice cold PBS, pelleted and mixed with 300 µl of propidium-iodide-buffer (containing 50 µg/ml PI in 0.1% sodium citrate plus 0.1% Triton X 100, Sigma) for 30 minutes at 4° C. Cell cycle analysis was performed as described previously (Nicoletti, I., Migliorati, G., Pagliacci, M. C., Grignani, F. & Riccardi, C. (1991) A rapid and simple method for measuring thymocyte apoptosis by propidium iodide staining and flow cytometry. *J Immunol Methods*, 139, 271-279) using a FACSCanto™ flow cytometer (BD Biosciences, Heidelberg, Germany).

Isolation of Primary AML Blasts and Cell Culture

BM- and PB-samples with heparin as anticoagulant were obtained from AML patients or donors with no evidence of malignant bone marrow infiltration after informed consent in a study approved by the local ethics committee. Mononuclear cells (MNC) were isolated immediately by means of Ficoll-Hypaque (Seromed, Berlin, Germany) density gradient centrifugation. For immunoblotting freshly isolated MNCs were either lysed directly or after incubation in RPMI 1640 supplemented with 20 mM Hepes (pH 7.3), 50 mM β-mercaptoethanol and 2 mM L-glutamine containing varying amounts of different tyrosine kinase inhibitors (PKC412, DHF125, DHF150). For cell cycle analysis, MNCs were maintained in RPMI 1640 medium supplemented as above plus 10% fetal calf serum (FCS).

Colony Assays

Bone-marrow MNCs were isolated as indicated above. Bone marrow samples were obtained from patients in CR after NHL or AML treatment or without evidence of any malignant bone marrow infiltration. $1 \times 10^5$ cells were plated in 1.1 ml Methocult™ (GF H4534) "Complete" Methylcellulose Medium with recombinant cytokines (StemCell Technologies, Vancouver, Canada) and incubated for 10 days at 37° C. in duplicate. Colony formation was counted on day 10.

Chemotherapeutic Agents

The chemotherapeutic agents cytarabine and daunorubicine were dissolved and diluted in aqua dest. Equivalent doses of DMSO were added when used for combination treatment.

Quantification of Synergism and Antagonism in Drug Combinations

For definition of synergism and/or antagonism in drug combinations we used the CompuSyn™ software (Chou, T C and Martin, N; ComboSyn, Inc. Paramus, N. J., USA) as previously described (Chou, T. C. (2006) Theoretical basis, experimental design, and computerized simulation of synergism and antagonism in drug combination studies. *Pharmacol Rev*, 58, 621-681).

Example 1

Figure 1B:
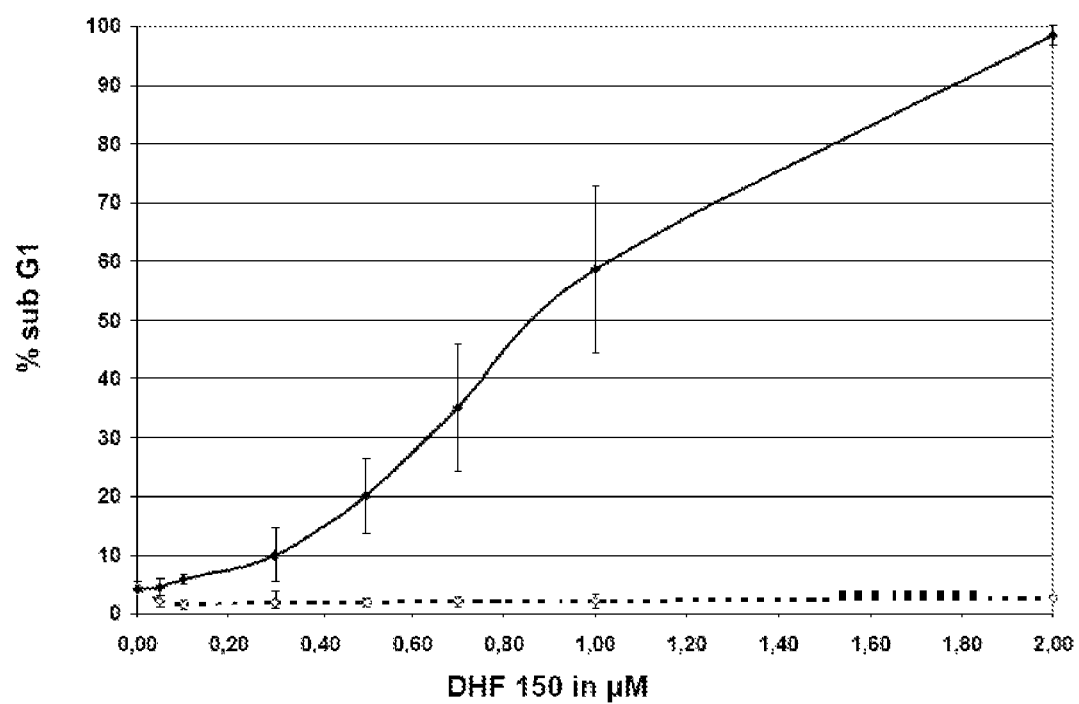
Figure 1C:
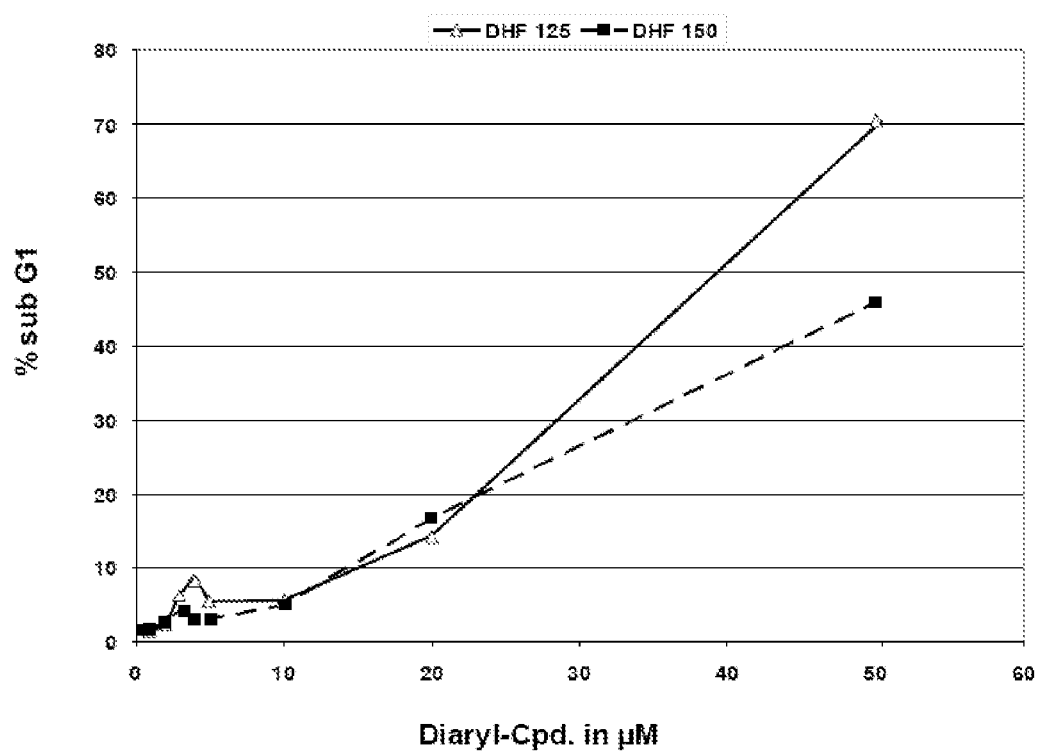

3-(Indolyl)- and 3-(azaindolyl)-4-phenylmaleimide derivatives induce apoptosis in murine 32D-FLT3-ITD cells The induction of apoptosis in murine 32D-FLT3-ITD cells measured by sub-G1-fraction in cell cycle analysis upon 48 h incubation with two 3-(indolyl)- and 3-(azaindolyl)-4-phenylmaleimide derivatives (DHF125 and DHF150) was evaluated. As shown in FIG. 1, treatment with DHF125 (FIG. 1A) and DHF150 (FIG. 1B) was associated with a statistically very significant dose-dependent increase of the sub-G1-cell fraction. No significant induction of apoptosis could be detected in FLT3-WT cells up to 10 µM of either compound (FIG. 1C), suggesting no significant toxicity within this range.

Example 2

Figure 2A:
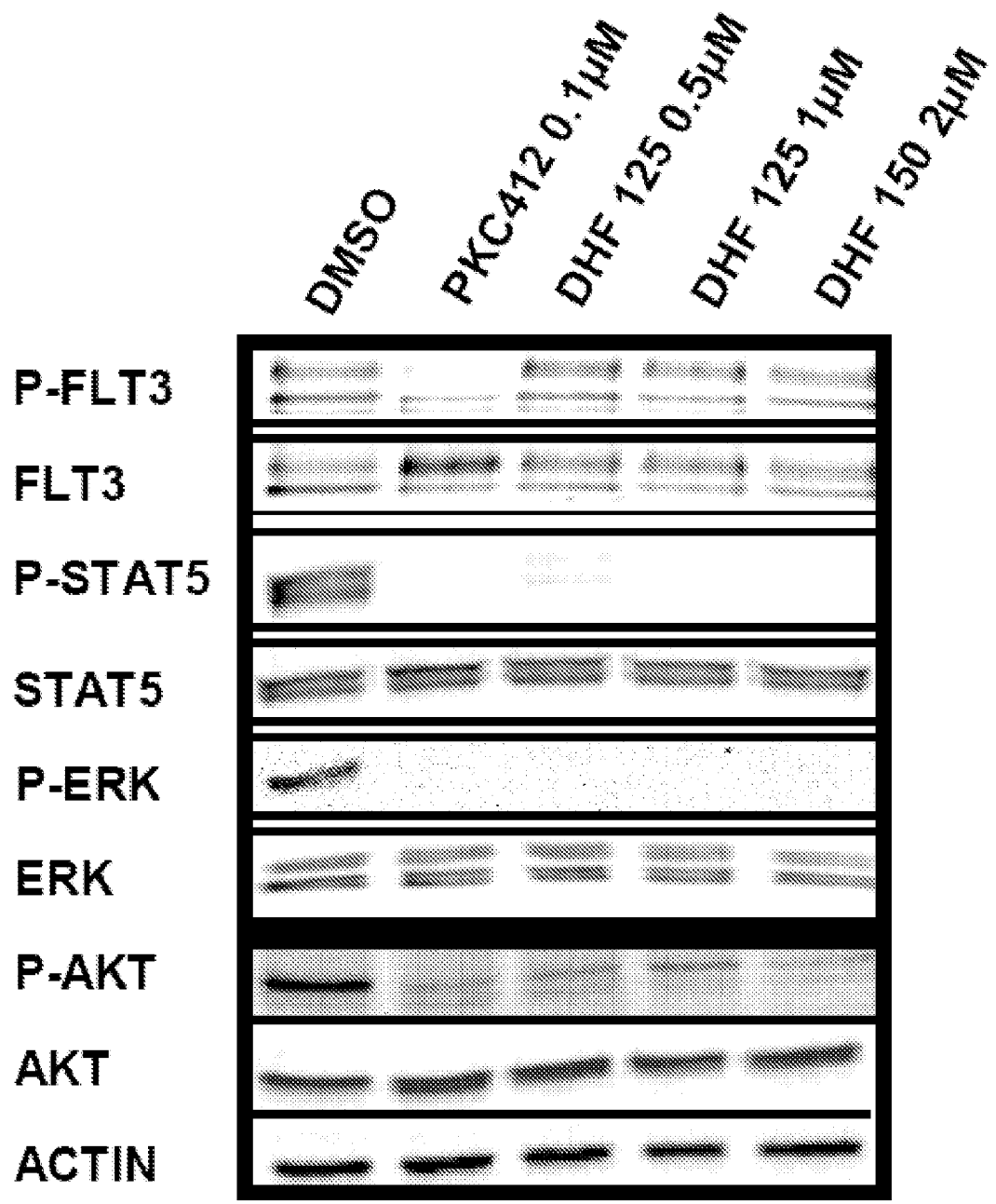
FIG. 2 shows (A) a Western Blotting of several kinase targets upon incubation with different concentrations of DHF125 and DHF150, and with the FLT3-tyrosine kinase inhibitor PKC412, compared to control (DMSO); (B) the activity of FLT3-kinase upon incubation with different concentrations of DHF125 and DHF150, in the presence of two ATP concentrations, compared to control (DMSO); and (C) immunoprecipitation of FLT3 (using anti-FLT3 and anti-P-Tyr) upon incubation with different concentrations of DHF125 and DHF150, in the presence of two ATP concentrations, compared to control (DMSO).
Figure 2B:
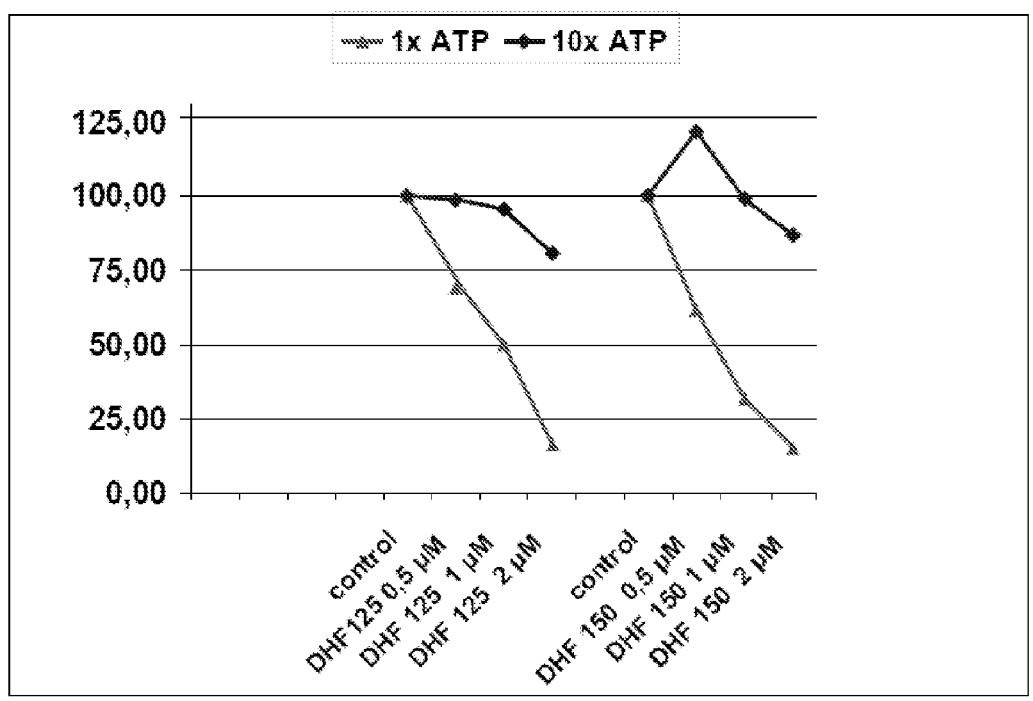
Figure 2C:
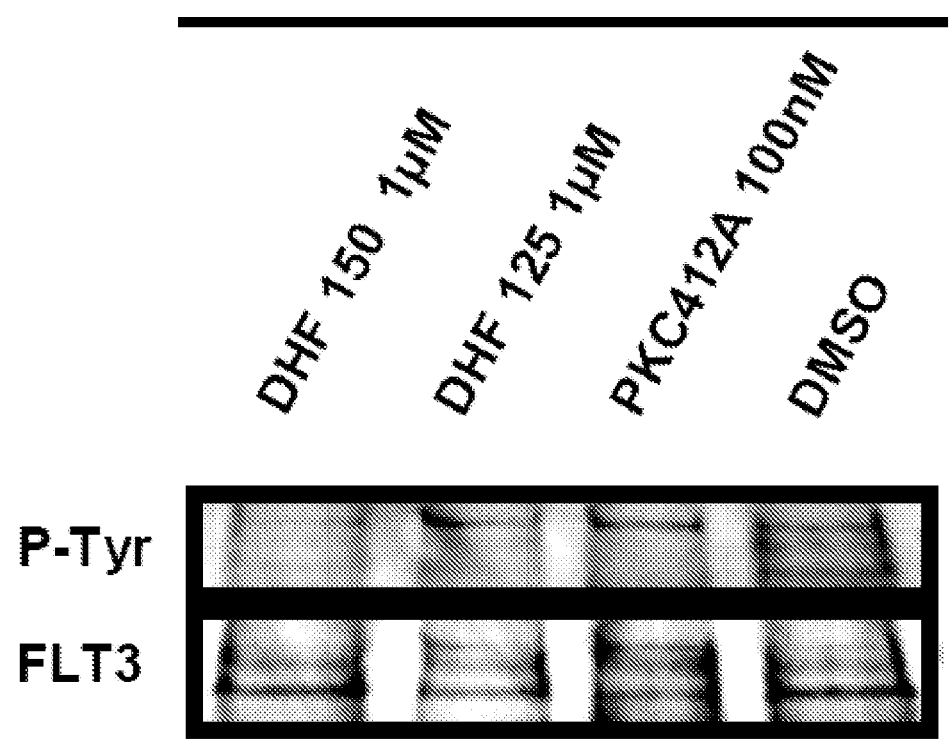

3-(Indolyl)- and 3-(azaindolyl)-4-phenylmaleimide3-(indolyl)- or 3-(azaindolyl)-4-phenylmaleimide derivatives inhibit FLT3-kinase Western Blotting comfirms dephosphorylation of downstream-targets STAT5, ERK and AKT (FIG. 2A). Using a FLT3-kinase assay, ATP competitive inhibition of FLT3-kinase could be demonstrated (FIG. 2B). Immunoprecipitation revealed dephosphorylation of FLT3 upon incubation with DHF125 and DHF150 (FIG. 2C).

Example 3

Figure 3:
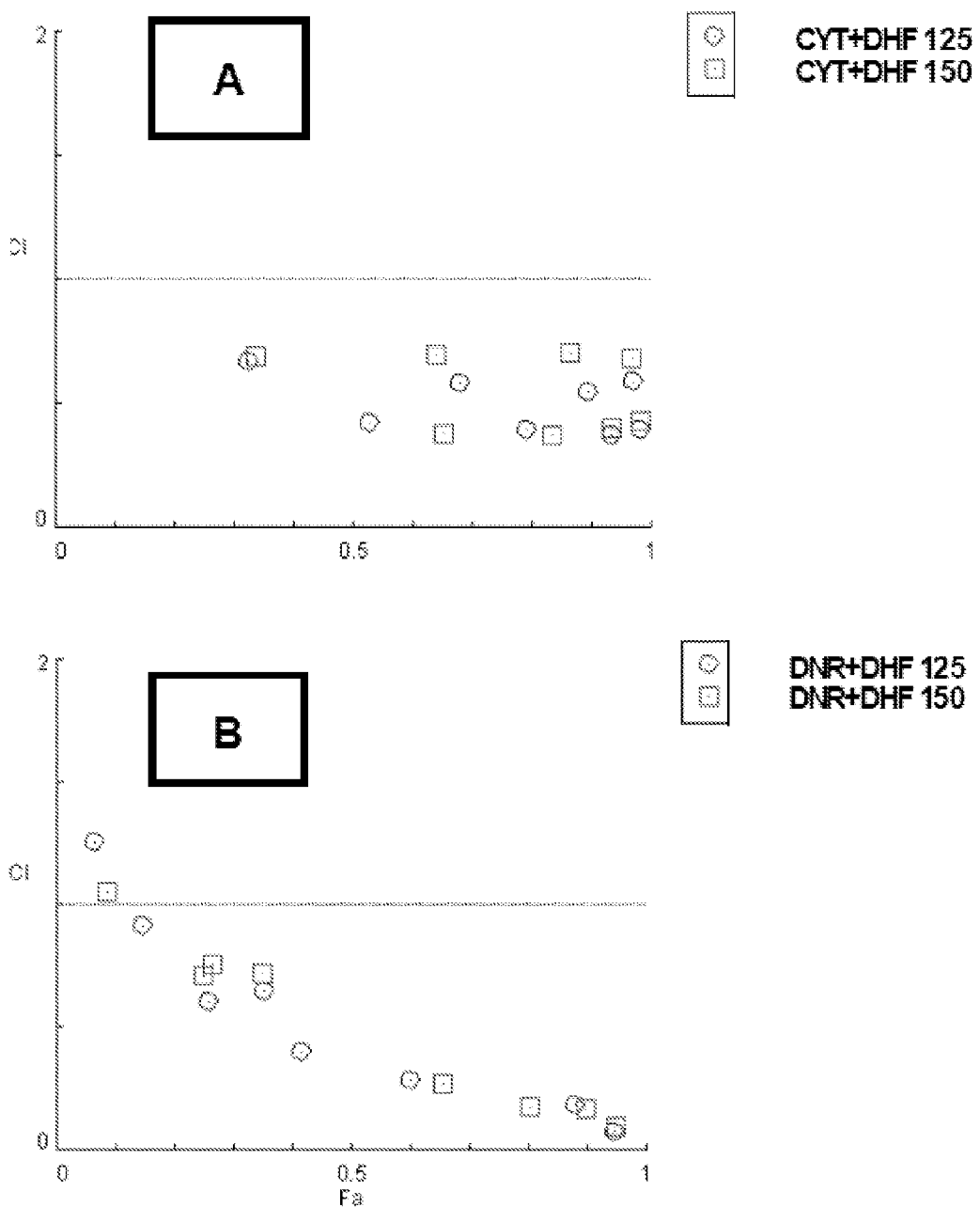
FIG. 3 is a Chou-Talalay-Plot showing the effects on FLT3-ITD-positive cells of DHF125 and DHF150, in combination with cytarabine (A) or daunorubicin (B).

3-(Indolyl)- and 3-(azaindolyl)-4-phenylmaleimide derivatives show efficacy in FLT3-ITD-positive cells and are synergistic in combination with chemotherapy Using a Chou-Talalay-Plot, synergistic effects of both compounds, DHF125 and DHF150, in combination with chemotherapy could be shown for cytarabine (FIG. 3A) and daunorubicine (FIG. 3B) using either compound.

Example 4

Figure 4A:
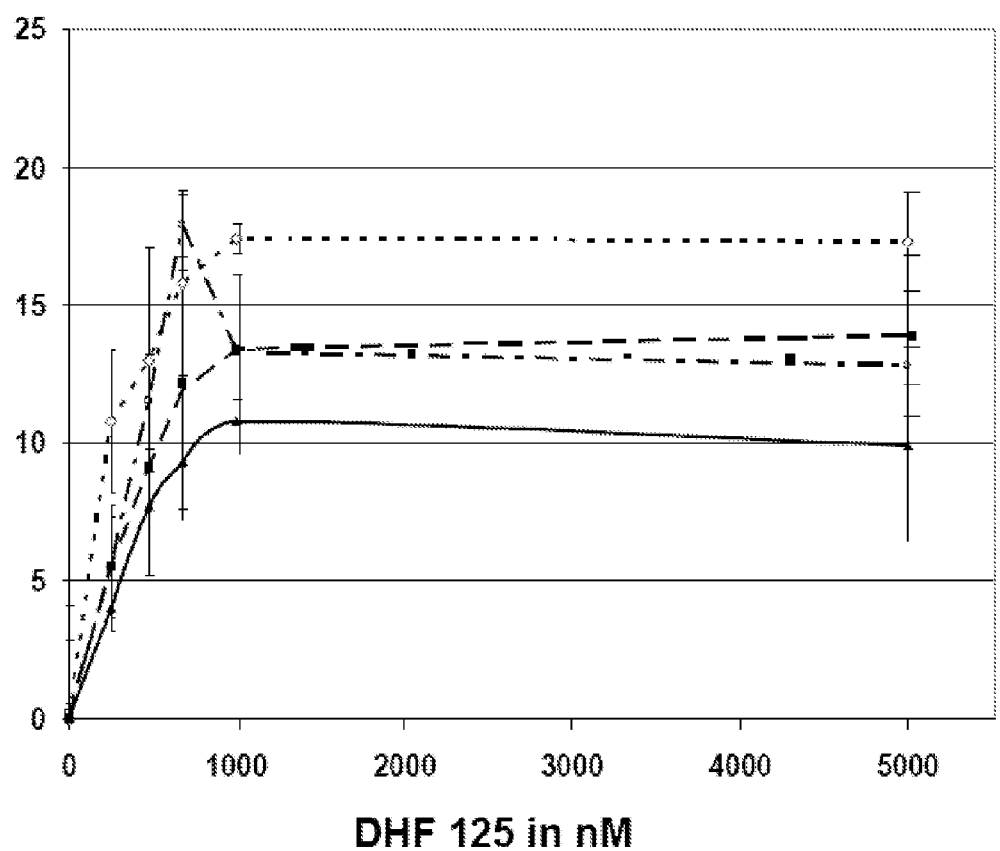
FIG. 4A shows DHF125.
Figure 4B:
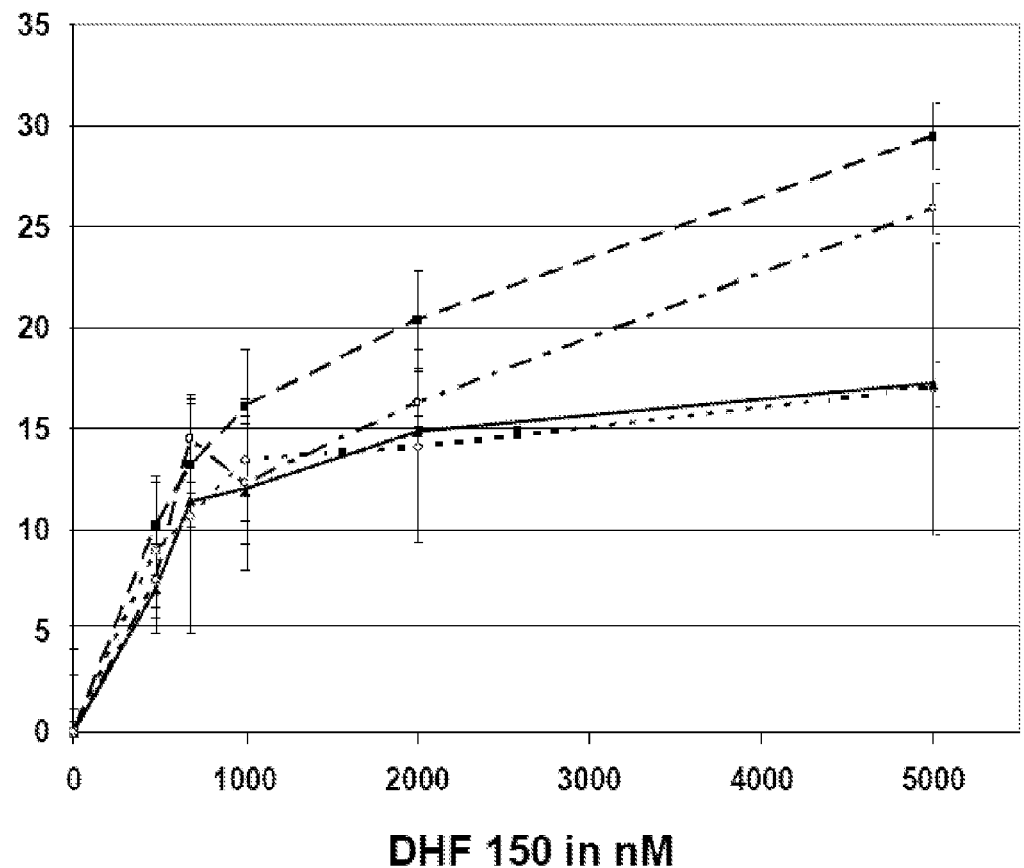
FIG. 4B shows DHF150.
Figure 5:
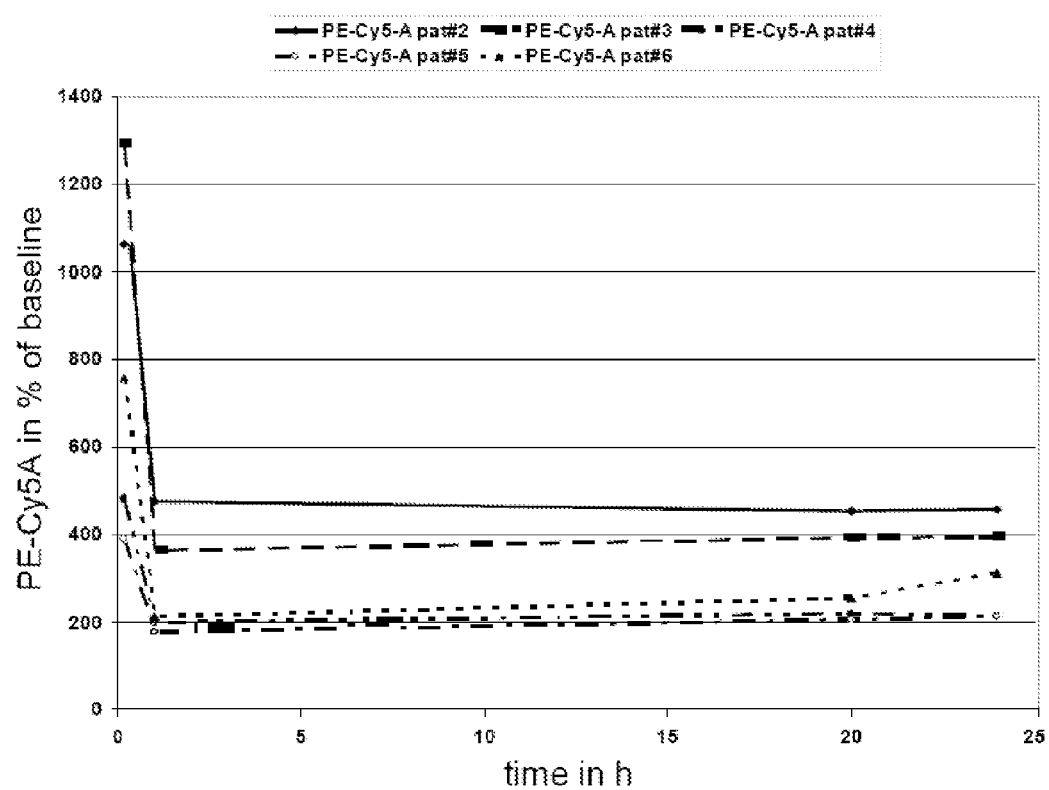
FIG. 5 shows uptake of DHF125 and DHF150 in primary AML blasts using FACS analysis (autofluorescence above baseline PE-Cy5A values).
Figure 6:
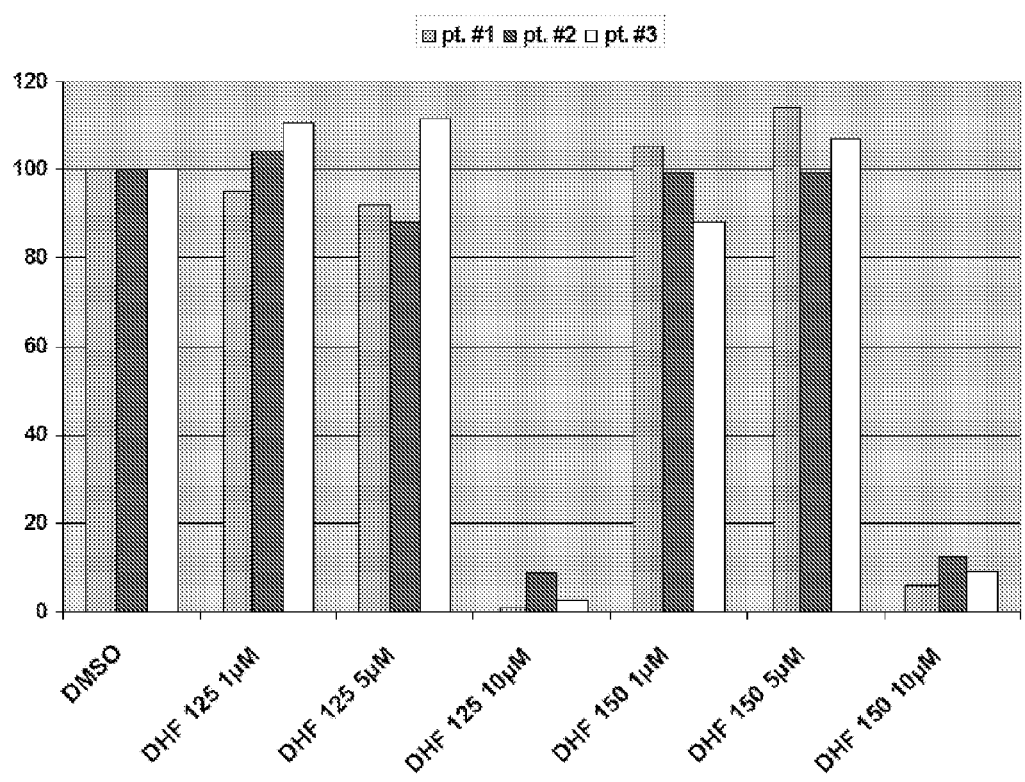
FIG. 6 is a diagram showing reduction in colony formation of non-malignant bone marrow cells upon incubation with different concentrations of DHF125 and DHF150.

3-(Indolyl)- and 3-(azaindolyl)-4-phenylmaleimide derivatives induce apoptosis in primary AML blasts Primary AML blasts at primary diagnosis were incubated for 72 h with both 3-(indolyl)- and 3-(azaindolyl)-4-phenylmaleimide derivatives. Induction of apoptosis was measured by sub-G1-fraction in FACS analysis. Percentage of apoptotic cells on top of ground apoptosis is shown for DHF125 (FIG. 4A) and DHF150 (FIG. 4B). Both compounds show induction of apoptosis of 10-17% (DHF125) and 17-28% (DHF150) in primary AML blasts harboring the FLT3-ITD mutation.

Example 5

3-(Indolyl)- and 3-(azaindolyl)-4-phenylmaleimide derivatives are taken up by primary AML blasts As both 3-(Indolyl)- and 3-(azaindolyl)-4-phenylmaleimide derivatives, DHF125 and DHF150, revealed autofluorescence, up-take could be evaluated in primary AML blasts using FACS analysis. Uptake occurred within 5 minutes and fluorescence of cells remained detectable after washing between 200-400% of baseline PE-Cy5A values for 24 hours. This suggests a rapid uptake and long term persistance in primary blasts.

Example 6

3-(Indolyl)- and 3-(azaindolyl)-4-phenylmaleimide derivatives do not inhibit colony formation of non-malignant bone marrow cells Both 3-(indolyl)- and 3-(azaindolyl)-4-phenylmaleimide derivatives, DHF125 and DHF150, showed no significant reduction in colony formation of non-malignant bone marrow cells up to 5 µM. Colony formation was reduced to a minimum using 10 µM of either compound, suggesting a myelotoxic effect.

Internal tandem duplication (ITD) mutations of FLT3 are present in leukemic blasts of approximately 30% of AML patients. ITD-mutations of FLT3 confer a worse prognosis and decreased overall survival. Therefore, FLT3-tyrosine kinase is considered an attractive drug target in AML and several FLT3-tyrosine kinase inhibitors (TKIs) are currently being tested in clinical trials (e.g., CEP701, MLN518, Sorafenib, PKC412).

As shown herein, two 3-(indolyl)- and 3-(azaindolyl)-4-phenylmaleimide derivatives inhibit FLT3 kinase in an ATP competitive manner. Moreover, dephosphorylation of FLT3 and of downstream-targets STAT5, ERK and AKT by DHF125 and DHF150 was observed.

The 3-(indolyl)- and 3-(azaindolyl)-4-phenylmaleimide derivatives of the present invention therefore qualify as FLT3-tyrosine kinase inhibitors.

The skilled artisan will be aware that apoptosis is a widely used restrictive mechanism, with the general picture now emerging that cells which are coerced into proliferation by forceful stimuli when they should not be in a proliferative stage will generally undergo apoptosis in order to save the organism, unless their apoptosis is blocked by some other effect. It is therefore to be expected that restoration of normal apoptosis capacity in cells which are running wild, will show an inclination to "understand, repent and die honourably", in particular where uncontrolled growth has already lead to a situation of biochemical stress. Such stress situations are known to be strongly pro-apoptotic stimuli.

As shown herein, two 3-(indolyl)- and 3-(azaindolyl)-4-phenylmaleimide derivatives strongly inhibit FLT3-ITD transfected 32D leukemic cells as well as primary ITD-positive AML blasts through the induction of apoptosis. On this basis, the 3-(indolyl)- and 3-(azaindolyl)-4-phenylmaleimide derivatives possess an antiproliferative effect on leukemic ells in vitro.

Using FLT3-tyrosine kinase inhibitors as monotherapy, against the setting of remarkable efficacy has emerged the problem of short duration of remission indicating rapid development of secondary resistance. In addition, up to 30% of patients may show primary resistance to currently available FLT3-TKIs.

As shown herein, the two 3-(indolyl)- and 3-(azaindolyl)-4-phenylmaleimide derivatives show synergistic effects in FLT3-ITD-positive cells when used in combination with cytarabine or daunorubicin. On this basis, the use of 3-(indolyl)- and 3-(azaindolyl)-4-phenylmaleimide derivatives in combination with chemotherapy is an attractive alternative for overcoming the limitations observed with the use of FLT3-tyrosine kinase inhibitors as monotherapy.

Thus, the 3-(indolyl)- and 3-(azaindolyl)-4-phenylmaleimide derivatives DHF125 and DHF150 and similar compounds of formula I, physiologically acceptable salts or solvates thereof as defined herein are useful in the treatment of leukemia, used as single therapeutics or in association with other chemotherapeutic agents.

The invention claimed is:

1. A method of treating leukemia in a subject in need of such treatment, or of preventing leukemia by arresting or reversing the progression of pre-leukemic cells to leukemic cell in a subject at risk of developing leukemia, wherein the method comprises administering an effective amount of a compound of formula I, or a physiologically acceptable salt thereof, or a physiologically acceptable solvate of the compound of formula I or of the physiologically acceptable salt thereof, to the subject

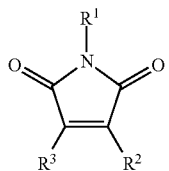

(I)

wherein
$R^1$ is H, $C_1$-$C_6$-alkyl, phenyl-$C_1$-$C_4$-alkyl or phenyl,
$R^2$ is a phenyl group which is substituted with 2 or 3 $C_1$-$C_6$-alkoxy groups and
$R^3$ is indolyl or azaindolyl which may carry one or two substituents independently selected from $C_1$-$C_6$-alkyl, $C_1$-$C_6$-alkoxy, phenyl, OH, halogen, $NH_2$, $C_1$-$C_6$-alkylamino, di-$C_1$-$C_6$-alkylamino, heteroaryl with 5 or 6 ring atoms containing 1 or 2 heteroatoms which are independently selected from O, N, and S, and heterocyclyl with 5 or 6 ring atoms containing 1 or 2 heteroatoms which are independently selected from O, N, and S, wherein the leukemia is characterized by leukemic cells which (i) show enhanced expression of FLT3, compared to non-malignant cells of the same cell type, or (ii) are positive for one or more than one activating mutation of the FLT3 gene.

2. The method of claim 1, wherein $R^1$ is H, $C_1$-$C_6$-alkyl, phenyl-$C_1$-$C_4$-alkyl or phenyl, $R^2$ is a phenyl group which is substituted with 2 or 3 $C_1$-$C_6$-alkoxy groups and $R^3$ is indolyl or azaindolyl which may carry one or two substituents independently selected from $C_1$-$C_6$-alkyl, $C_1$-$C_6$-alkoxy, and phenyl.

3. The method of claim 1, wherein $R^2$ is a group having the formula

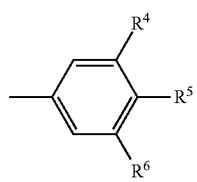

wherein two of the radicals $R^4$, $R^5$ and $R^6$ are $C_1$-$C_6$-alkoxy and the third of the radicals $R^4$, $R^5$ and $R^6$ is H or $C_1$-$C_6$-alkoxy.

4. The method of claim 3, wherein $R^4$ and $R^5$ are $C_1$-$C_6$-alkoxy and $R^6$ is H; or $R^4$, $R^5$ and $R^6$ are $C_1$-$C_6$-alkoxy.

5. The method of claim 1, wherein $R^3$ is selected from:

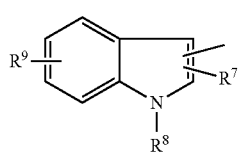

a)

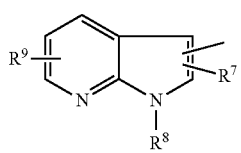

b)

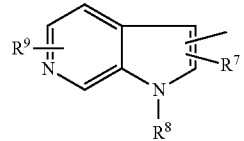

c)

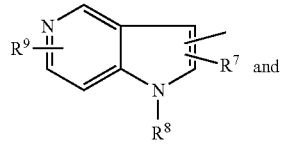

d) and

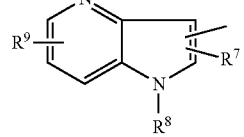

e)

wherein $R^7$ is H, $C_1$-$C_6$-alkyl or phenyl, $R^8$ is H, $C_1$-$C_6$-alkyl or phenyl and $R^9$ is H, $C_1$-$C_6$-alkyl, $C_1$-$C_6$-alkoxy, OH, halogen, $NH_2$, $C_1$-$C_6$-alkylamino, di-$C_1$-$C_6$-alkylamino, heteroaryl with 5 or 6 ring atoms containing 1 or 2 heteroatoms which are independently selected from O, N, and S, or heterocyclyl with 5 or 6 ring atoms containing 1 or 2 heteroatoms which are independently selected from O, N, and S.

6. The method of claim 5, wherein $R^9$ is H, $C_1$-$C_6$-Alkyl or $C_1$-$C_6$-Alkoxy.

7. The method of claim 5, wherein $R^7$, $R^8$ and $R^9$ are H.

8. The method of claim 1, wherein $R^1$ is H.

9. The method of claim 5, wherein groups (a) to (e) are attached to the maleimide group via the 3-position of the indole group.

10. The method of claim 1, wherein the compound of formula I is a compound of formula Ia

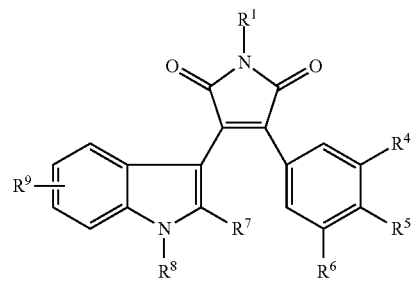

(Ia)

wherein:
$R^1$ is H, $C_1$-$C_6$-alkyl, phenyl-$C_1$-$C_4$-alkyl or phenyl;
$R^4$ and $R^5$ are $C_1$-$C_6$-alkoxy and $R^6$ is H; or $R^4$, $R^5$ and $R^6$ are $C_1$-$C_6$-alkoxy;
$R^7$ is H, $C_1$-$C_6$-alkyl or phenyl;
$R^8$ is H, $C_1$-$C_6$-alkyl or phenyl; and
$R^9$ is H, $C_1$-$C_6$-alkyl, $C_1$-$C_6$-alkoxy, OH, halogen, $NH_2$, $C_1$-$C_6$-alkylamino, di-$C_1$-$C_6$-alkylamino, heteroaryl with 5 or 6 ring atoms containing 1 or 2 heteroatoms which are independently selected from O, N, and S, or heterocyclyl with 5 or 6 ring atoms containing 1 or 2 heteroatoms which are independently selected from O, N, and S.

11. The method of claim 1, wherein the compound of formula I is a compound of formula Ib

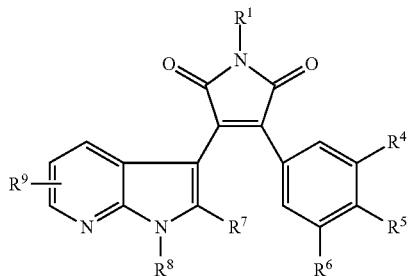

wherein:
R$^1$ is H, C$_1$-C$_6$-alkyl, phenyl-C$_1$-C$_4$-alkyl or phenyl;
R$^4$ and R$^5$ are C$_1$-C$_6$-alkoxy and R$^6$ is H; or R$^4$, R$^5$ and R$^6$ are C$_1$-C$_6$-alkoxy;
R$^7$ is H, C$_1$-C$_6$-alkyl or phenyl;
R$^8$ is H, C$_1$-C$_6$-alkyl or phenyl; and
R$^9$ is H, C$_1$-C$_6$-alkyl, C$_1$-C$_6$-alkoxy, OH, halogen, NH$_2$, C$_1$-C$_6$-alkylamino, alkylamino, heteroaryl with 5 or 6 ring atoms containing 1 or 2 heteroatoms which are independently selected from O, N, and S, or heterocyclyl with 5 or 6 ring atoms containing 1 or 2 heteroatoms which are independently selected from O, N, and S.

12. The method of claim 1, wherein the compound of formula I is 3-(indole-3-yl)-4-(3,4,5-trimethoxyphenyl)-1H-pyrrole-2,5-dione, 3-(7-azaindol-3-yl)-4-(3,4,5-trimethoxyphenyl)-1H-pyrrole-2,5-dione, or a physiologically acceptable salt thereof, or a physiologically acceptable solvate of the compound or of the physiologically acceptable salt thereof.

13. The method of claim 1, wherein the leukemia is acute myelogenous leukemia.

14. The method of claim 1, wherein the leukemia is refractory leukemia.

15. The method of claim 1, wherein the leukemia is resistant leukemia.

16. The method of claim 1, wherein the leukemia is positive for the internal tandem duplication in the juxtamembrane domain of the fms-like tyrosine kinase receptor-3 gene (FLT3-ITD).

17. The method of claim 1, further comprising administering a further chemotherapeutic agent to the subject.

18. The method of claim 17, wherein the further chemotherapeutic agent is selected from the group consisting of cytarabine, etoposide, mitoxantron, cyclophosphamide, retinoic acid, daunorubicin, doxorubicin and idarubicin.

19. The method of claim 1, which is a method of treating leukemia in a subject which comprises administering an effective amount of a compound of formula I, a physiologically acceptable salt thereof, or a physiologically acceptable solvate of the compound of formula I or of the physiologically acceptable salt thereof, to a subject in need of such treatment.

20. The method of claim 19, wherein the method comprises administering an effective amount of a compound of formula I or a physiologically acceptable salt thereof, to a subject in need of such treatment.

* * * * *